(12) United States Patent
Derkx et al.

(10) Patent No.: US 10,945,628 B2
(45) Date of Patent: Mar. 16, 2021

(54) APPARATUS AND METHOD FOR PROCESSING ELECTROMYOGRAPHY SIGNALS RELATED TO RESPIRATORY ACTIVITY

(71) Applicant: KONINKLIJKE PHILIPS N.V., Eindhoven (NL)

(72) Inventors: Rene Martinus Maria Derkx, Eindhoven (NL); Jakob Van Der Laar, Oosterhout (NL); Adrianus Johannes Maria Denissen, Moergestel (NL); Sandrine Magali Laure Devot, Cologne (DE)

(73) Assignee: Koninklijke Philips N.V., Eindhoven (NL)

( * ) Notice: Subject to any disclaimer, the term of this patent is extended or adjusted under 35 U.S.C. 154(b) by 456 days.

(21) Appl. No.: 15/752,147

(22) PCT Filed: Aug. 1, 2016

(86) PCT No.: PCT/EP2016/068261
§ 371 (c)(1),
(2) Date: Feb. 12, 2018

(87) PCT Pub. No.: WO2017/025363
PCT Pub. Date: Feb. 16, 2017

(65) Prior Publication Data
US 2018/0235503 A1 Aug. 23, 2018

(30) Foreign Application Priority Data

Aug. 11, 2015 (EP) .................................... 15180614

(51) Int. Cl.
*A61B 5/0488* (2006.01)
*A61B 5/00* (2006.01)
*A61B 5/08* (2006.01)

(52) U.S. Cl.
CPC .............. *A61B 5/0488* (2013.01); *A61B 5/08* (2013.01); *A61B 5/6823* (2013.01);
(Continued)

(58) Field of Classification Search
CPC ..... A61B 5/0488; A61B 5/6833; A61B 5/721; A61B 5/08; A61B 5/6823; A61B 5/0816; A61M 2230/40
See application file for complete search history.

(56) References Cited

U.S. PATENT DOCUMENTS 5,800,470 A 9/1998 Stein
6,015,388 A * 1/2000 Sackner ................. A61B 5/411
600/529

(Continued)

FOREIGN PATENT DOCUMENTS

WO 199846129 A1 10/1998
WO 2013045920 A1 4/2014

(Continued)

OTHER PUBLICATIONS

Murphy, P.B. et al., "Neural respiratory drive as a physiological biomarker to monitor change during acute exacerbations of COPD", Thorax 2011, 56:502-508.

(Continued)

*Primary Examiner* — Sean P Dougherty
(74) *Attorney, Agent, or Firm* — Daniel H. Brean (57) ABSTRACT

The present invention relates to the field of medical technology and in particular to determining a respiratory activity in patients with chronic obstructive pulmonary disease (COPD) based on surface electromyography measurements taken from the intercostal muscles on the chest of a subject. A processing apparatus for processing an electromyography signal indicative of an activity of a target muscle in a human or animal body that relates to the measurement of respiratory (Continued)

effort amid an activity of at least one further muscle is presented. The processing apparatus comprises a first interface for receiving a first electromyography signal obtained from the target muscle and the further muscle at a first location on the body; a second interface for receiving a second electromyography signal obtained from the further muscle at a second location on the body; and an analysis unit for determining a similarity signal based on the first electromyography signal and the second electromyography signal, wherein the analysis unit is further configured to determine a respiratory phase as an inspiratory phase if the similarity signal obtained from the first and the second electromyography signal is below a first predetermined threshold and/or determine a respiratory phase as an expiratory phase if the similarity signal obtained from the first and the second electromyography signal exceeds a second predetermined threshold.

16 Claims, 5 Drawing Sheets

(52) U.S. Cl.
CPC ............ *A61B 5/6833* (2013.01); *A61B 5/721* (2013.01); *A61B 5/7246* (2013.01); *A61B 5/0816* (2013.01); *A61M 2230/40* (2013.01)

(56) References Cited

U.S. PATENT DOCUMENTS

| | | | |
|---|---|---|---|
| 6,588,423 B1 | 7/2003 | Sinderby | |
| 2003/0226565 A1 | 12/2003 | Sinderby | |
| 2005/0085734 A1* | 4/2005 | Tehrani | A61N 1/3601 600/484 |
| 2006/0282131 A1 | 12/2006 | Caparso | |
| 2009/0159082 A1* | 6/2009 | Eger | A61M 16/026 128/204.23 |
| 2012/0095742 A1 | 4/2012 | Heyer | |
| 2013/0116520 A1 | 5/2013 | Roham | |
| 2013/0171599 A1* | 7/2013 | Bleich | A63B 15/00 434/247 |
| 2013/0310699 A1 | 11/2013 | Hart | |
| 2013/0345585 A1 | 12/2013 | Samy | |
| 2014/0187995 A1 | 7/2014 | Hu | |
| 2014/0276167 A1 | 9/2014 | Dasgupta | |
| 2016/0100808 A1* | 4/2016 | Anbarani | A61B 5/087 600/324 |
| 2016/0310069 A1* | 10/2016 | Sinderby | A61B 5/7246 |

FOREIGN PATENT DOCUMENTS

| | | |
|---|---|---|
| WO | 2015044010 A1 | 4/2015 |
| WO | 2015089668 A1 | 6/2015 |
| WO | 2016120074 A1 | 8/2016 |

OTHER PUBLICATIONS

Murphy, P.B. et al "Chronic Obstructive Pulmonary Disease, Neural Respiratory Drive as a Physiological Biomarker to Monitor change during Acute Exacerbations of COPD", Thorax 2011, pp. 602-608.
Widrow, B. et al "Adaptive Noise Cancelling: Principles and Applications", Proc. IEEE, vol. 63, 1975, pp. 1672-1716.
Han, J.N. et al., "Respiratory function of the rib cage muscles," Eur Respir J, vol. 6, pp. 722-728, 1993.
Bartolo, A. et al, "Analysis of diaphragm EMG signals: comparison of gating vs. subtraction for removal of ECG aontamination", Journal of Applied Physiology, vol. 80, No. 6, pp. 1898-1902, Jun. 1996.
M.L. Duiverman, et.al., "Reproducibility and responsiveness of a non-invasive EMG technique of the respiratory muscles in COPD patients and in healthy subjects", J. Appl. .Physiol., Dec. 5, 2003.
Paul Munyard, et.al, "A New Device for Ambulatory Cough Recording", Pediatric Pulmonology, 18:178-186 (1994).
Dal Vecchio, L. et al, ""Intrinsic" positive end-expiratory pressure in stable patients with chronic obstructive pulmonary disease," Eur Respir J, vol. 3, pp. 74-80, 1990.
De Troyer, A. et al., "Respiratory Action of the Intercostal Muscles", Physiol Rev, vol. 85, pp. 717-756, 2005.

\* cited by examiner

APPARATUS AND METHOD FOR PROCESSING ELECTROMYOGRAPHY SIGNALS RELATED TO RESPIRATORY ACTIVITY

CROSS-REFERENCE TO PRIOR APPLICATIONS

This application claims the priority benefit under 35 U.S.C. § 371 of International Patent Application No. PCT/EB2016/068261, filed on Aug. 1, 2016, which claims the priority benefit of European Patent Application No. 15180614.8, filed on Aug. 11, 2015, the contents of which are herein incorporated by reference.

FIELD OF THE INVENTION

The present invention relates to the field of medical technology and in particular to determining a respiratory activity in patients with chronic obstructive pulmonary disease (COPD) based on surface electromyography measurements taken from the intercostal muscles on the chest of a subject. The present invention relates to an apparatus and method for processing an electromyography signal as well as a to a corresponding computer program for carrying out said method.

BACKGROUND OF THE INVENTION

Electromyography (EMG) is a technique for determining an activity of a muscle. An electromyography system detects an electrical potential generated by muscle cells when these cells are electrically or neurologically activated. An electrode or a pair of electrodes for differential measurement is applied to a target muscle to obtain a voltage signal indicative of an activity of the muscle.

Signals can either be measured directly within the muscle (invasive EMG) or on the skin above the muscle (surface EMG). For invasive EMG, a needle electrode is directly inserted into the muscle tissue of interest. For surface EMG, as a non-invasive technique, an electrode is applied to the skin of the subject.

Surface EMG measurements involve the detection, processing and recording of very small electrical variations generated by muscle tissue. These signals can be as low as only a few microvolts in amplitude and can therefore be subject to interference from other more dominant noise sources, either from the measurement system or from the human body itself.

One application of surface EMG is determining a respiratory activity at the parasternal region of the chest that is used to assess the neural respiratory drive (NRD) in patients with chronic obstructive pulmonary disease (COPD) or other respiratory diseases. A respiratory activity may be calculated using an electromyography measurement from the parasternal intercostal muscles.

WO 2013/045920 A1 discloses a corresponding patient monitoring method and monitoring device. A neural respiratory drive (NRD) is measured by obtaining a measure of the second intercostal space parasternal electromyogram. Signals are acquired using conventional electrodes and amplifiers. For improving the EMG signal it is suggested to apply a filtering algorithm to remove electrocardiogram (ECG) artifacts from the EMG signal. A high pass filter is applied to the raw signal to remove base line noise and additional band pass filtering between 12-20 Hz is performed to remove respiration artifacts.

Murphy et al., "Neural respiratory drive as a physiological biomarker to monitor change during acute exacerbations of COPD", p. 602-608, Thorax 2011, also teaches monitoring the neural respiratory drive (NRD) by measuring second intercostal space parasternal electromyography (EMG) activity. The analysis uses a root mean squared (RMS) EMG signal. Nasal cannulae are connected to a differential pressure transducer (Validyne DP 45, Validyne, Northridge, Calif. USA) in order to identify inspiratory and expiratory phases of breathing.

Murphy et al. further teaches that contamination from other chest wall muscles cannot be excluded. Therefore, patient position and electrode position are carefully observed during data acquisition to maximize the contribution of the second intercostal space parasternal muscle to the inspiratory EMG signal and to minimize activity of other muscles. Furthermore, Murphy et al. teaches that a needle electrode technique could be used to isolate parasternal muscle activity.

US 2012/0095742 A1 discloses a system and method for processing signals for the real-time detection of a functional cyclic activity. A position of aquisition means, such as EMG electrodes, on the patient is validated based on a correlation score between two signals from two acquisiton means.

Correspondingly, WO 2015/089668 A1 discloses a method and system for validating inspiratory muscle activity of a patient and a mechanical ventilation system using the same.

U.S. Pat. No. 6,588,423 B1 discloses a method and device for triggering ventilatory support responsive to myoelectrical activity. A logic trigger circuit triggers ventilatory support in relation to a myoelectrical signal, resporatory flow signal and/or respiratory pressure signal to assist respriation of a patient. The amplitude of the myoelectrical signal is compared to a given threshold, and ventilatory support is triggered when the amplitude of the myoelectrical signal is higher than this threshold.

SUMMARY OF THE INVENTION

It is an object of the present invention to further improve an electromyography system. In particular, it would be advantageous to analyze the breathing process in more detail, in particular for COPD patients who increasingly use accessory muscles to breathe.

In a first aspect of the present invention a processing apparatus for processing an electromyography signal indicative of an activity of a target muscle in a human or animal body that relates to the measurement of respiratory effort amid an activity of at least one further muscle is presented. The processing apparatus comprises a first interface for receiving a first electromyography signal obtained from the target muscle and the further muscle at a first location on the body;

a second interface for receiving a second electromyography signal obtained from the further muscle at a second location on the body; and an analysis unit for determining a similarity signal based on the first electromyography signal and the second electromyography signal, wherein the analysis unit is further configured to determine a respiratory phase as an inspiratory phase if the similarity signal obtained from the first and the second electromyography signal is below a first predetermined threshold and/or determine a respiratory phase as an expiratory phase if the similarity signal obtained from the first and the second electromyography signal exceeds a second predetermined threshold.

In a further aspect of the present invention a method for processing an electromyography signal indicative of an activity of a target muscle in a human or animal body that relates to the measurement of respiratory effort amid an activity of at least one further muscle is presented. The method comprises the steps of:

receiving a first electromyography signal obtained from the target muscle and the further muscle at a first location on the body;

receiving a second electromyography signal obtained from the further muscle at a second location on the body;

determining a similarity signal based on the first electromyography signal and the second electromyography signal; and determining a respiratory phase as an inspiratory phase if the similarity signal obtained from the first and the second electromyography signal is below a first predetermined threshold and/or determining a respiratory phase as an expiratory phase if the similarity signal obtained from the first and the second electromyography signal exceeds a second predetermined threshold.

In a further aspect of the present invention a further processing apparatus for processing an electromyography signal indicative of an activity of a target muscle in a human or animal body that relates to the measurement of respiratory effort amid an activity of at least one further muscle is presented. The processing apparatus comprises:

a first interface for receiving a first electromyography signal obtained from the target muscle and the further muscle at a first location on the body;

a second interface for receiving a second electromyography signal obtained from the further muscle at a second location on the body;

an analysis unit for determining a similarity signal based on the first electromyography signal and the second electromyography signal, wherein the analysis unit is further configured to provide, based on the similarity signal, a respiratory phase signal indicative of the respiratory phase; and wherein the processing apparatus is further configured to determine a respiratory effort based on the respiratory phase signal and the first electromyography signal.

In a further aspect of the present invention a further method for processing an electromyography signal indicative of an activity of a target muscle in a human or animal body that relates to the measurement of respiratory effort amid an activity of at least one further muscle is presented. The method comprises the steps of:

receiving a first electromyography signal obtained from the target muscle and the further muscle at a first location on the body;

receiving a second electromyography signal obtained from the further muscle at a second location on the body;

determining a similarity signal based on the first electromyography signal and the second electromyography signal; and providing, based on the similarity signal, a respiratory phase signal indicative of the respiratory phase; and determining a respiratory effort based on the respiratory phase signal and the first electromyography signal.

In a further aspect of the present invention a further method for processing an electromyography signal indicative of an activity of a target muscle in a human or animal body that relates to the measurement of respiratory effort amid an activity of at least one further muscle is presented. The method comprises the steps of:

receiving a first electromyography signal obtained from the target muscle and the further muscle at a first intercostal space;

receiving a second electromyography signal obtained from the further muscle at a second intercostal space;

determining a similarity signal based on the first electromyography signal and the second electromyography signal.

In a further aspect of the present invention an electromyography system comprising an electromyography device comprising one of the aforementioned processing apparatuses is presented. The system can further comprise a first pair of electrodes for obtaining the first electromyography signal, wherein the first pair of electrodes is connectable to a first input of the electromyography device for providing the first electromyography signal to the first interface of the processing apparatus; and a second pair of electrodes for obtaining the second electromyography signal, wherein the second pair of electrodes is connectable to a second input of the electromyography device for providing the second electromyography signal to the second interface of the processing apparatus.

In further aspects of the present invention, there are provided a computer program which comprises program code means for causing a computer to perform the steps of one of the methods disclosed herein when said computer program is carried out on a computer, as well as an non-transitory computer-readable recording medium that stores therein a computer program product, which, when executed by a processor, causes one of the methods disclosed herein to be performed.

Preferred embodiments of the invention are defined in the dependent claims. It shall be understood that the claimed method has similar and/or identical preferred embodiments as the claimed device and as defined in the dependent claims.

The herein presented solutions provide a possibility to further improve an electromyography system. In particular, aspects of the proposed solutions provide the possibility to analyze the breathing process in more detail, in particular in COPD patients who increasingly use accessory muscles to breathe.

The prior art suggests measuring an electromyography signal obtained at the second intercostal space, i.e. a measurement of the parasternal muscles between the second and third costal cartilages, which prolong the ribs forward. However, a surface EMG measurement provides a measurement of not only the activity of the desired parasternal intercostals but actually of a mixture activity of at least three major muscles located at the parasternal region, namely the parasternal intercostal muscles (in particular an interchondral part of the internal intercostal muscles, involved during inspiration), the transversus thoracis muscles (accessory muscles of expiration), and the pectoralis major. The pectoralis major can be heavily activated during trunk and arm movements such as posture change, resulting in motion artifact in the EMG measurement. If not well relaxed, e.g. if excessively used to maintain posture, the pectoralis major muscle can also generate in the measurement an undesired activity of tonic nature. It can possibly also generate in the measurement an activity of phasic nature, if recruited during forced inhalation.

The prior art (Murphy et al.) instructs the patient to keep still and relaxed, which reduces a contribution of the pectoralis major muscle, and further teaches that an invasive needle electrode technique could be used to isolate parasternal muscle activity. While invasive EMG can provide excellent results in terms of signal quality, the application of needles into the body of the subject is very inconvenient and in particular not practical for a home healthcare setting.

The inventors follow a different approach in that in addition to a conventional electromyography signal, a second electromyography signal is obtained at a second location on the body. While the first electromyography signal is obtained from the target muscle and a further muscle, the second electromyography signal is obtained from the further muscle at a second location on the body which does not provide a signal from the target muscle. In other words, the second electromyography signal is obtained from the further muscle but not from the target muscle of the first electromyography signal. It should be noted that there might be a residual contribution from the target muscle due to cross talk which may be tolerated. By introducing the measurement of the second electromyography signal, an activity of different muscles, in particular an activity of a parasternal intercostal muscle as the target muscle and an activity of a transversus thoracis muscle as the further muscle, can be distinguished.

The present invention is based on the recognition that nerve and, consequently, activity of one intercostal muscle or muscle portion, e.g. the second intercostal space parasternal muscle, is essentially independent of the activity of another intercostal muscle or muscle portion, e.g. independent of the third intercostal space parasternal muscle, or another intercostal muscle portion at the second intercostal space. At first glance such an independence may seem counterintuitive, since the second intercostal space parasternal muscle and the third intercostal space parasternal muscle may contract in a synchronized manner to support breathing e.g. in healthy subjects but even more COPD patients. Nonetheless, it has been found that the motor unit action potentials can be essentially independent, they can superpose randomly/arbitrarily.

Other muscles, however, like the transversus thoracis and the pectoralis major span across multiple intercostal spaces along the sternum. As a result if a muscle activity is measured at at least two locations on the body such that at least one intercostal muscle is measured as the target muscle at the first location only and at least one further muscle that spans the two locations is measured at both locations, a similarity of the two measurements can be determined as a similarity signal over time. If only or predominantly the target muscle is active, a similarity between the first electromyography signal obtained from the target muscle and the further muscle at the first location on the body and the second electromyography signal obtained from the further muscle is low, however if the further muscle is active, the similarity between the first and the second electromyography signal can be high. The additional electromyography signal thus provides additional information to distinguish between different muscle activity types. The similarity can be indicative of a respiratory phase and/or of a tonic muscle activity. For example, an activity of a parasternal intercostal muscle can be distinguished from an activity of the transversus thoracis muscle. Based thereon it is then possible to distinguish between inspiratory and expiratory activity. In an embodiment, the internal intercostals can be seen as a muscle of expiration, the external intercostals can be seen as a muscle of inhalation. As another example, an activity of a parasternal intercostal muscle can be distinguished from an activity of the pectoralis major muscle. Based thereon it is then possible to distinguish between phasic and tonic activity.

Therefore, the analysis unit can be configured to determine a respiratory phase as an inspiratory phase if the similarity signal obtained from the first and the second electromyography signal is below a first predetermined threshold and/or to determine a respiratory phase as an expiratory phase if the similarity signal obtained from the first and the second electromyography signal exceeds a second predetermined threshold. The first predetermined threshold and the second predetermined threshold can be the same or different. It has been found that an inspiratory effort due to the intercostal muscles provides a substantially uncorrelated or independent signal due to the separate innervation of the respective muscles for example obtained at the second intercostal space as the first location and the third intercostal space as the second location. The electromyography signals thus show a low correlation which can be represented as a low value of the similarity signal. The expiratory effort, which can be attributed to an activity of the transversus thoracis muscles, in turn produces a correlated signal since the transversus thoracis muscles stretch underneath the second and third intercostal spaces. The electromyography signals thus show a high correlation which can be represented as a high value of the similarity signal. It is thus possible to distinguish between the in- and expiratory effort.

As used herein the term 'electromyography signal' can refer to a potential or voltage signal indicative of an activity of a muscle. An electromyography signal can be obtained as a single-ended measurement of one electrode with respect to a reference potential. However, advantageously, a differential measurement is performed using a pair of EMG electrodes, in particular surface EMG electrodes. In particular for surface EMG measurements, an electromyography signal can represent a superposition of the action potentials of one or more underlying muscles.

As used herein the term 'muscle' can refer to a single muscle, but can also refer to a set of muscles belonging to the same muscle-type or a set of muscles addressing the same function. For example, when referring to an intercostal muscle this can include intercostal muscles that are close to the sternum, e.g. the parasternal muscles, but also further away from the sternum, e.g. the external intercostals or the interosseous part of the internal intercostals. Also the intercostal muscle can be located in the $2^{nd}$ intercostal space, but can also be located in the $3^{rd}$ intercostal space. For simplicity, reference can thus be made to the intercostal muscle.

As used herein the term 'similarity signal' can refer to a signal indicative of a similarity between the first electromyography signal and the second electromyography signal. This similarity signal can be indicative of how the first electromyography signal is related to the second electromyography signal, no matter if there is a scaling factor, which can include a sign-flip. Such a similarity can be computed, for example, by means of a cross-correlation or coherence, in particular spectral coherence, between the first and second electromyography signal. Thereby, an analysis of a relation between the first and second electromyography signal can be performed over time.

As used herein the term 'breathing effort' or 'respiratory effort' can refer to the effort that has to be made in particular by patients suffering from respiratory diseases such as COPD in order to sustain the ventilatory demand or expression, i.e. the drive to breathe. In particular, the breathing effort can describe a respiratory muscle activity, such as an activity of the parasternal intercostal muscles or transversus thoracis muscles to support breathing. A respiratory muscle activity can also be referred to as phasic activity in contrast to tonic activity of a muscle.

In an embodiment the target muscle can be an intercostal muscle, in particular a parasternal intercostal muscle. The further muscle can be a transversus thoracis or pectoralis major. It has been found that the parasternal intercostal muscles can be activated to support inhalation. A level of activity of the parasternal internal intercostal muscles can thus be indicative of a breathing effort intensity during inhalation. An evaluation of the activity of the intercostal muscles can also serve as an indicator of day-to-day deterioration or improvement of COPD patients. The transversus thoracis, also referred to as the triangularis sterni muscle, on the other hand can be activated for non-passive expiration. The transversus thoracis muscles may be recruited for a forced expiration because COPD patients who experience expiratory flow limitation and may want to push air out of their lungs as much as they can prior to the inspiratory phase. The pectoralis major in turn is related to trunk and/or arm movements of the subject, as well as posture maintenance, and not primarily related to respiration. Advantageously, the patient is instructed to remain still and keep the muscles relaxed during the measurement to avoid motion artifacts and keep the measured tonic activity as low as possible. Additional sensory measurements, for example from an accelerometer, can also be used to identify motion artifacts for example to omit the breathing effort assessment measurement in such cases. Possibly, the pectoralis major may also be involved during forced inspiration.

In an embodiment the similarity signal is indicative of a (cross-)correlation or spectral coherence of the first electromyography signal and the second electromyography signal. The similarity of the first electromyography signal and the second electromyography signal can in turn be indicative of a respiratory phase of the subject because during different phases of the respiratory cycle different muscles are involved. In healthy subjects at rest, respiration is mainly performed by the diaphragm. In patients with respiratory disorder, such as COPD, inspiration can be assisted incrementally by the parasternal intercostal muscles and by additional accessory muscles. Since the intercostal muscles in the second intercostal space and the intercostal muscles in the third intercostal space are separately innervated, the corresponding action potentials are substantially independent for a first electromyography signal obtained at the second intercostal space and a second electromyography measurement at the third intercostal space. On the other hand, the underlying *triangularis* sterni muscles also called the transversus thoracis muscles which stretch beyond the second and the third intercostal spaces produce a correlated signal which is present in both the first electromyography signal at the second intercostal space and in the second electromyography signal at the third intercostal space. Hence, the first and second electromyography signals are not similar (or not correlated) when the respective intercostal muscles are active during inhalation whereas the first and second electromyography signals are similar or correlated when the transversus thoracis muscles are active during non-passive expiration.

In an embodiment at least one of the first electromyography signal and the second electromyography signal is obtained at an intercostal space. Advantageously the first electromyography signal is obtained at one of the intercostal spaces and the second electromyography signals is obtained at another intercostal space.

In an embodiment the first electromyography signal is obtained at the second intercostal space and/or the second electromyography signal is obtained at the third intercostal space. The second intercostal space refers to the intercostal space between the second and the third costal cartilage or rib. The third intercostal space refers to the intercostal space between the third and the fourth costal cartilage or rib. Hence, the first electromyography signal provides a signal reading of the parasternal intercostal muscles between the second and third costal cartilage as well as the underlying transversus thoracis, whereas the second electromyography signal provides a signal reading of the parasternal intercostal muscles between the third and fourth costal cartilage as well as the underlying transversus thoracis. Hence, different intercostal muscles contribute to the first and second electromyography signals whereas the same transversus thoracis muscle or group of muscles contributes to the first and the second electromyography signal.

In an embodiment the first electromyography signal can be obtained from the further muscle and a first instance of the target muscle at the first location on the body and the second electromyography signal is obtained from the further muscle and a second instance of the target muscle at the second location on the body. The target muscle can refer to a group of muscles such as the parasternal intercostal muscles. Instances of the target muscle can refer to different locations where these muscles can be found. For example, the first instance of the target muscle can be the second intercostal space parasternal muscles, i.e. the parasternal intercostal muscles in the second intercostal space, whereas the second instance of the target muscle can be the third intercostal space parasternal muscles, i.e., the parasternal intercostal muscles in the third intercostal space. However, the first and second electromyography signals are obtained from the same further muscle or group of muscles, such as the transversus thoracis. In a further example, the first instance of the target muscle can be the second intercostal space parasternal muscles, i.e., the intercostal muscles located close to the sternum in the second intercostal space, whereas the second instance of the target muscle can be another muscle or muscle portion located in the second intercostal space but not close to the sternum, i.e., further away from the sternum, for example the internal intercostals excluding the interchondral part or the external intercostals. In this embodiment, the further muscle can be the pectoralis major muscle which spans across the locations and is then measured at both the first and second locations. An activity of the pectoralis major can thus be present in both the first electromyography signal and the second electromyography signal. It is assumed that the activity of this muscle leads to a correlated signal for the first and second location, whereas the activity of the parasternal intercostal muscles leads to an uncorrelated signal for the first and second location. Hence, whether the pectoralis major is recruited to maintain posture or change posture, the similarity signal can be indicative of tonic/postural activity, including body motions. While the pectoralis major has been used as an example, the disclosure is not limited thereto.

In an embodiment, the analysis unit is configured to determine, based on the similarity signal, a respiratory phase.

In an embodiment the analysis unit is further configured to provide, based on the similarity signal, a respiratory phase signal indicative of the respiratory phase. The processing apparatus can be further configured to determine a breathing effort based on the respiratory phase signal and the first electromyography signal. An advantage of this embodiment is that the determined respiratory phase can be provided to subsequent signal processing stages. A further advantage is that the respiratory effort can be determined for different phases of the respiration cycle. Thereby, the respiratory problems of a patient can be analyzed in more detail which can beneficial for subsequent therapy.

Advantageously the processing apparatus is configured to determine an inspiratory effort during an inspiratory phase and/or to determine an expiratory effort during an expiratory phase. In a further refinement, the processing apparatus is configured to determine an inspiratory effort based on a signal energy of the first electromyography signal during an inspiratory phase and/or to determine an expiratory effort based on a signal energy of the first electromyography signal during an expiratory phase. The determination can be based on an RMS (root mean square) value of the EMG signal. A corresponding analysis can also be performed based on the second electromyography signal for example provided that the second electromyography signal is also originating from a measurement location at an intercostal space. An advantage of this embodiment is that the inspiratory and/or expiratory effort of the patient can be quantified for example for comparing these values with thresholds indicative of a malignant state of the patient.

In an embodiment the processing apparatus is configured to remove, based on the similarity signal, an activity of the further muscle from the first electromyography signal. Advantageously an activity of the further muscle can be removed, for example in case of tonic activity, whether it is present to maintain or change posture, for example indicated by a high similarity of the first and second electromyography signals due to an activity of the pectoralis major as the further muscle. In a most basic configuration, the activity of the further muscle can be removed by blanking out periods of the first electromyography signal. For example, the first electromyography signal can be set to zero when a time localized activity of the further muscle is determined based on the similarity signal. Hence, undisturbed signal portions of the first electromyography signal can be used for further signal processing.

In an embodiment the processing apparatus is configured for removing from the first electromyography signal a dependent signal that originally is present in both the first electromyography signal and the second electromyography signal. An advantage of this embodiment can be that, for example, a contribution which is due tonic activity produced by the (not relaxed) pectoralis major muscle to maintain posture can be eliminated. A voltage signal due to the pectorals major muscle is expected to provide an EMG reading with much larger amplitude than the underlying intercostal muscles. An advantage of this approach is that an otherwise hidden signal can be shown. Advantageously this approach goes beyond the mere differential measurement wherein the second electromyography signal would simply be subtracted from the first electromyography signal to obtain a difference signal. Adaptive filters can be used to remove unwanted signals from a mixture of wanted and unwanted signals by using the second electromyography signal as a reference signal for the adaptive filter. Principles of adaptive noise cancelling are explained by B. Widrow et. al., "Adaptive Noise Cancelling: Principles and Applications", Proc. IEEE, Vol. 63, 1975, pp. 1692-1716.

In yet another aspect of the present invention an electrode patch for use with the afore-mentioned processing apparatus is presented. The electrode patch comprises at least two sets of electrodes for surface electromyography measurements at at least two different locations on the chest, wherein a first set of electrodes comprises a first pair of electrodes for measuring a first electromyography signal at a first intercostal space besides the sternum; and wherein a second set of electrodes comprises a second pair of electrodes for measuring a second electromyography signal at a second intercostal space besides the sternum. Advantageously, the first pair of electrodes can comprise a first electrode and a second electrode, the second pair of electrodes can comprise a third electrode and a fourth electrode. The first electrode and the second electrode of the electrode patch can be arranged for measuring the first electromyography signal at the second intercostal space, i.e. between the second and third costal cartilages on both sides of the sternum; whereas the third and fourth electrode of the electrode patch can be arranged for measuring the second electromyography signal at the third intercostal space, i.e., between the third and fourth costal cartilages on both sides of the sternum. In a further example, the first electrode and the second electrode of the electrode patch can be arranged for measuring the first electromyography signal at the second intercostal space besides the sternum, i.e., between the second and third costal cartilages on both sides of the sternum; whereas the third and fourth electrodes of the electrode patch can be arranged for measuring the second electromyography signal at the second intercostal space, i.e., between the second and third costal ribs on both sides of the sternum, but further away from the sternum. This can be advantageous for determining an activity of the pectoralis major.

An advantage of this particular arrangement of electrodes in a single patch is that it facilitates electrode placement. In view of patient diversity regarding geometrical dimensions, the arrangement of the electrode locations is defined with respect to anatomical features. The predetermined arrangement of the electrodes with respect to each other also reduces the risk of placing the electrodes at a wrong location. Thereby, the electrode placement does not necessarily have to be performed by highly trained medical personnel but can also be performed by a user for example in a home healthcare setting.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
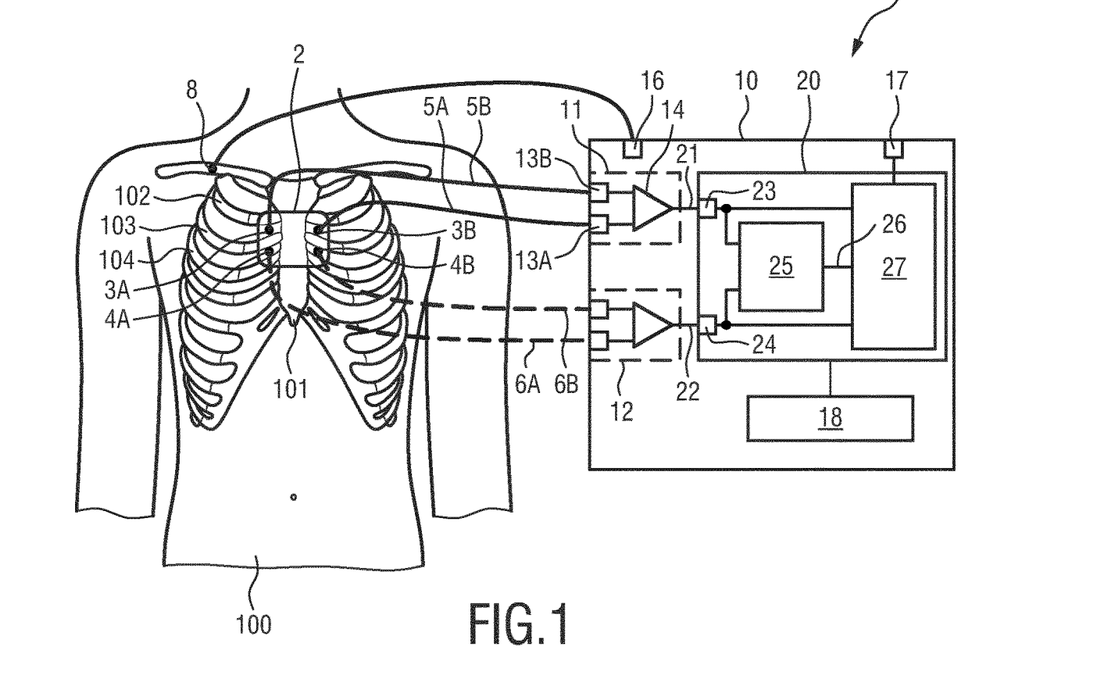
FIG. 1 shows an electromyography system according to an aspect of the present invention applied to a subject.

FIG. 1 shows an embodiment of an electromyography system applied to a body of a subject. The electromyography system is therein denoted in its entirety with reference numeral 1.

The electromyography system 1 in this embodiment comprises an electromyography device 10 which in turn comprises a processing apparatus 20 for processing an electromyography signal, in particular an for processing an electromyography signal indicative of an activity of a target muscle in a human or animal body that relates to the measurement of respiratory effort due to activity of parasternal intercostal muscles amid an activity of at least one further muscle.

The processing apparatus 20 comprises a first interface 23 for receiving a first electromyography signal 21 obtained from the target muscle and the further muscle at a first location on the body; a second interface 24 for receiving a second electromyography signal 22 obtained from another instance of the target muscle and the further muscle at a second location on the body; and an analysis unit for determining a similarity signal based on the first electromyography signal 21 and the second electromyography signal 22. In the present non-limiting example, the target muscle is a parasternal intercostal muscle, the further muscle is a transversus thoracis muscle, the first location on the body is the second intercostal space 105 (FIG. 5) between the second costal 102 and the third costal 103, and the second location on the body is the third intercostal space 106 (FIG. 5) between the third costal 103 and the fourth costal 104.

Figure 3:
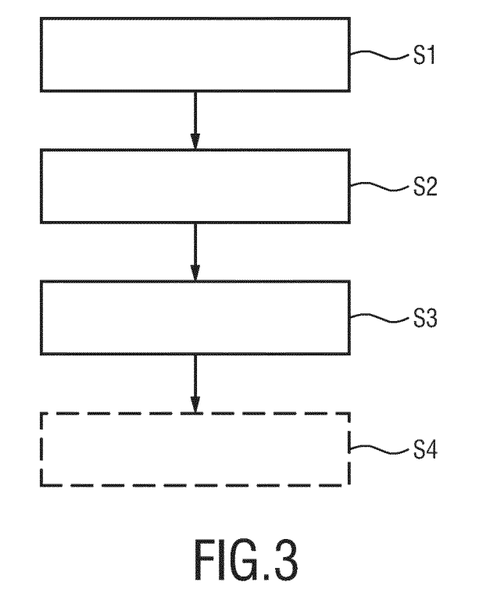
FIG. 3 shows a flow chart of a method for processing electromyography signals according to an aspect of the present invention.

A corresponding method for processing an electromyography signal indicative of an activity of a target muscle in a human or animal body that relates to the measurement of respiratory effort amid an activity of at least one further muscle is depicted in FIG. 3. In a first step S1, a first electromyography signal obtained from the target muscle and the further muscle at a first location on the body is received. In a second step S2, a second electromyography signal obtained from the further muscle at a second location on the body is received. In a third step S3, a similarity signal is determined based on the first electromyography signal and the second electromyography signal. In an optional fourth step S4, a respiratory phase can be determined based on the similarity signal. For example, a respiratory phase can be determined as an inspiratory phase if the similarity signal obtained from the first and the second electromyography signal is below a first predetermined threshold and/or a respiratory phase can be determined as an expiratory phase if the similarity signal obtained from the first and the second electromyography signal exceeds a second predetermined threshold.

The electromyography system 1 further comprises a first pair of electrodes 3A, 3B for obtaining the first electromyography signal 21, wherein the first pair of electrodes is connectable to a first input 11 of the electromyography device 10 for providing the first electromyography signal 21 to the first interface 23 of the processing apparatus 20; and a second pair of electrodes 4A, 4B for obtaining the second electromyography signal 22, wherein the second pair of electrodes is connectable to a second input 12 of the electromyography device 10 for providing the second electromyography signal 22 to the second interface 24 of the processing apparatus 20.

The first and second pairs of electrodes 3A, 3B, 4A, 4B are provided by an electrode patch 2 for application to the skin on the chest of the subject 100. Hence, the electrode patch 2 comprises two sets of electrodes 3A, 3B and 4A, 4B for differential surface electromyography measurements at at least two different locations on the chest of the subject 100, here along the sternum of the subject 100. The first set of electrodes thus comprises the first pair of electrodes 3A, 3B for measuring the first electromyography signal 21 at a first parasternal intercostal space, here the intercostal space between the second costal cartilage or rib 102 and the third costal 103. The first electrode 3A and the second electrode 3B of the first pair of electrodes are connected to a first input 11 of the electromyography device 10 via a pair of electrode leads 5A, 5B. Correspondingly, the third electrode 4A and the fourth electrode 4B of the second pair of electrodes are connected to a second input 12 of the electromyography device 10 via a pair of electrode leads 6A, 6B.

The electromyography device 10 can optionally further comprise a ground interface 16 for a connection to an optional further electrode 8 also referred to as a reference electrode or ground electrode at an electrically neutral place, in particular a bony prominence, on the body of the subject 100.

The electromyography device can further comprise an output unit 18. The output unit 18 can for example be a human machine interface (HMI) such as a display unit or can also be a communication interface for wired or wireless communication with further devices such as a hospital information system (HIS), an electronic health record (EHR), a computer or smartphone for providing results of the signal processing of the processing apparatus 20 and/or for visualizing the electromyography signals.

In patients with chronic obstructive pulmonary disease (COPD) and other respiratory diseases, the assessment of the parasternal muscle activity measured from surface EMG, for example with electrodes positioned at the second intercostal space 105 between the second costal 102 and third costal 103, can be useful to estimate an intensity, timing and duration of a respiratory effort of a patient as an indicator of a balance between respiratory muscle load and respiratory muscle capacity. The imbalance between muscle load and muscle capacity often observed in COPD patients is caused by several effects. For example, the respiratory muscle pump load is increased by increased resistance, elastic and threshold loads. The muscle capacity can be decreased by hyperinflation of the lungs, and functional diaphragm weakness. It has been found that RMS EMG, advantageously measured parasternally at the second intercostal space, that occurs during inhalation is related to the neural respiratory drive (NRD). In COPD patients, with increasing lung hyperinflation as observed during acute exacerbation, there is a change in the balance between respiratory muscle load and capacity, which is reflected by a lower capacity and higher load resulting in increased NRD.

As shown in FIG. 1 a respiratory muscle activity at the second intercostal space 104 can be measured via two EMG electrodes 3A, 3B located symmetrically on both sides of the sternum 101, i.e., at a parasternal location. The two electrodes can be mounted on a single EMG electrode patch 2, which also eases the placement of the electrodes. It has been found that the electrodes at the second intercostal space 105 mainly measure the inspiration breathing effort due to the activation of the parasternal intercostal muscles during inhalation.

It has further been found that via two EMG electrodes 3A, 3B, a measure of the maximum power of the electromyogram (EMG) measured at the second intercostal space 105 parasternal muscles during inhalation can be used as an indicator of day-to-day deterioration/improvement of a COPD patient when multiple measurements are performed over a number of days, and as a predictor of hospital readmission after discharge as well. The inspiratory peaks in RMS EMG can be used, for example an inspiratory peak RMS EMG activity averaged over a predetermined time such as 1 minute. To accommodate day-to-day electrode placement differences, differences in thickness of sub-cutaneous fat-tissue and differences in thickness of pectoralis major muscles, normalization can be done with so-called 'sniff' readings. During a sniff reading, the patient is instructed to perform one or more sniff maneuvers as a quick forced inspiratory sniff (as strong as they can) for calibration.

Hence, such EMG-based measures can be used as an objective marker of respiratory function and support safe and early discharge of a patient. This is of particular relevance for US and UK hospitals, because the hospital has to pay the additional cost for the patient, in case the patient is readmitted to the hospital with the same problem within a predetermined period of time such as one month.

It is known that the measurement of the EMG signal at the second intercostal space can also be contaminated by cardiac activity. Hence, known techniques for removal of contaminations due to a cardiac activity, i.e. ECG (electrocardiogram) removal techniques, can be applied to obtain a signal only reflecting the EMG without cardiac activity. The electromyography device 10 can optionally comprise a further interface 17, for example for receiving a motion signal to avoid a measurement in case of motion artifacts. A motion signal can be obtained with an optional accelerometer. Optionally an accelerometer can be comprised in the electromyography device 10 in case the electromyography device is attached to the body of the patient. Alternatively, the accelerometer can be comprised in the EMG electrode patch.

Referring again to the electromyography device 10 of FIG. 1, an input 11 can comprise a first connector 13A and a second connector 13B for connection to the electrode leads 5A, 5B of the electrodes 3A, 3B of the electrode patch 2. Thereby, the electrodes can be connected for example to a differential amplifier 14 in particular a high impedance differential amplifier which provides a differential electromyography signal 21 at its output. The second input 12 of the electromyography device 10 can be configured accordingly for providing the second electromyography signal 22.

Figure 2:
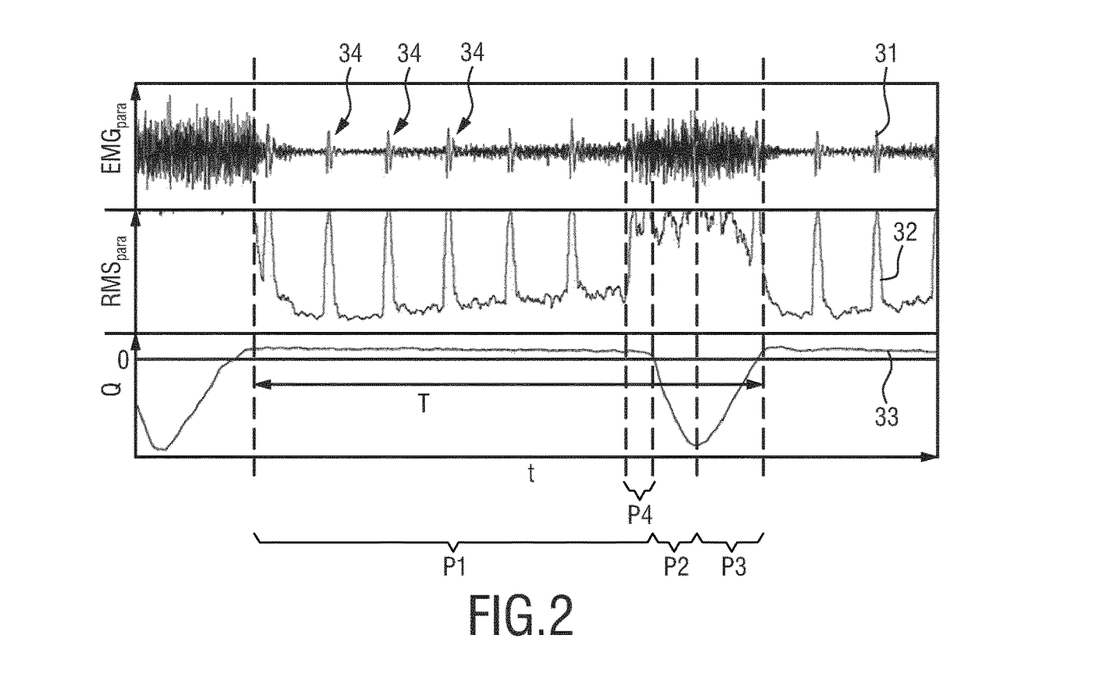
FIG. 2 shows exemplary graphs of a raw electromyography signal, an RMS electromyography signal, and a respiratory flow.

FIG. 2 illustrates exemplary graphs of a raw electromyography signal 31, an RMS electromyography signal 32, and a respiratory flow 33.

The top graph of FIG. 2 shows a raw EMG signal 31 of a parasternal EMG measurement, $EMG_{para}$. The vertical axis denotes an EMG voltage in microvolts, whereas the horizontal axis denotes the time tin seconds. The depicted signal trace represents a first electromyography signal 21 obtained as a differential EMG measurement using a single pair of EMG electrodes 3A, 3B arranged at the second parasternal intercostal space 105 of the subject 100.

The middle graph of FIG. 2 shows the root mean squared (RMS) electromyography signal 32. The vertical axis denotes the RMS value, corresponding to the top graph, whereas the horizontal axis again denotes the time tin seconds. For a parasternal measurement this value is also referred to as $RMS_{para}$ as described by Murphy et al.

The bottom graph shows a graph of a differential pressure signal Q 33 that has been measured with nasal/oral cannulae as a reference for the respiratory activity. The vertical axis denotes the pressure signal Q, whereas the horizontal axis denotes the time tin seconds.

As shown in the top graph of FIG. 2, the raw EMG signal not only comprises influences due to breathing but also crosstalk from cardiac activity as exemplarily denoted by reference numeral 34. Such cardiac activity can be removed by ECG removal techniques. ECG removal can advantageously be performed as a preprocessing step by the processing apparatus 20.

Referring now to the bottom graph of FIG. 2, an entire breathing cycle is denoted by T. The breathing cycle can further be divided into a first period P1 where expiration occurs and a second period including P2 and P3 where inspiration occurs.

As it can be seen from the lower two graphs in FIG. 2, the $RMS_{para}$ signal 32 and Q signal 33 do not show fully synchronized characteristics during the expiratory phase P1 and the inspiratory phase P2 and P3.

The measurement relates to a COPD patient. Besides the inspiratory effects due to the parasternal intercostal muscles, expiratory effects are also being measured as shown in the traces 31, 32. In particular, during the expiratory phase P1, it can be seen that some muscle activity builds up in the $RMS_{para}$ signal 32. Furthermore, FIG. 2 shows that EMG activity already significantly increases prior to the actual inspiration phase P2 and P3. This is denoted by P4. What can be interpreted as the recruitment of inspiratory muscles starts before the actual pressure drop at the nose and the airflow generation, truly indicative of inspiration. A first possible explanation is that COPD patients have to overcome an intrinsic positive end-expiratory pressure (PEEP) before being able to generate airflow. However, there can be a mixture of contributions in the $RMS_{para}$ signal 32, with superposition of forced expiratory activity, as the increase energy in the $RMS_{para}$ signal 32 during P1 seems to indicate. Hence, inspiration and expiration cannot easily be distinguished based on the EMG measurement 31 from a single pair of electrodes 3A, 3B located at the second intercostal space 105.

In other words, the first electromyography signal 31 not only reflects an activity of the second intercostal space parasternal muscles 105 but actually provides a mixture of different muscle activities, in particular an inspiratory phasic activity of the parasternal muscle which is active during quiet inspiration; an expiratory phasic activity, which can be of the transversus thoracis muscles possibly activated during non-passive expiration, and a tonic activity of for example the pectoralis major, which is activated during posture change, posture maintenance and the like. A contribution of the pectoralis major can be reduced by instructing the patient to remain still and as relaxed as possible, since this muscle can be controlled voluntarily.

Hence, there is a need (a) to distinguish between the inspiration phase P2 and P3 and the expiration phase P1, for example to capture the inspiratory breathing effort and (b) to determine the source and nature of the EMG activity, for example tonic or phasic activity. Because each muscle has a specific physiological function, there is a need to distinguish between the different muscle types, especially the parasternal muscle activity versus the activity of the transversus thoracis muscle for extracting the relevant information from the EMG signal at the parasternal location. Thereby, one or more objective markers of respiratory function in particular for COPD patients or other pulmonary diseases can be determined.

In order to clearly attribute an EMG activity to the parasternal intercostal muscles, the prior art suggests the use of the needle electrode technique to isolate parasternal muscle activity. In contrast to the prior art, the inventors suggest the use of a second electromyography signal 22. It has been found, that a second electromyography signal can used to distinguish between different muscle activity types involved in the breathing process.

Referring again to FIG. 1, in an embodiment, in addition to the first pair of surface EMG electrodes 3A, 3B, a second pair of surface EMG electrodes 4A, 4B is provided for obtaining the second electromyography signal 22. The processing apparatus 20 of the EMG device 10 thus comprises a second interface 24 for receiving the second electromyography signal 22 which is obtained at a second location 106 on the body 100.

In the given example, the second pair of EMG electrodes 4A, 4B is positioned at the second intercostal space 106 between the third costal 103 and a fourth costal 104. At first glance, the second electromyography signal 22 may seem to behave analogous to the first electromyography signal 21, because the third intercostal space 106 also includes parasternal intercostal muscles that can be involved during inspiratory breathing effort. However, it has been found that these parasternal muscles running from the third costal 103 to the fourth costal 104 are independently innervated compared to the parasternal intercostal muscles at the second intercostal space 105 which runs from the second costal 102 to the third costal 103.

Figure 4:
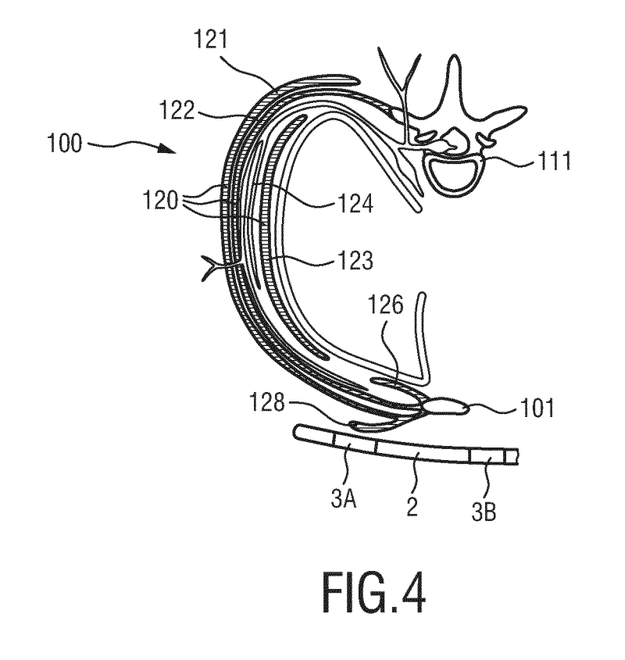
FIG. 4 shows an anatomical sketch of the innervation of the parasternal intercostal muscles.

FIG. 4 shows an anatomic sketch of the chest of a body 100 at the second intercostal space 105 in a transverse body plane. FIG. 4 shows the bone structures of the sternum 101 and the spine 111. Regarding the intercostal muscles, FIG. 4 shows the external intercostal muscle 121, the internal intercostal muscle 122 and the innermost intercostal muscle 123 which together are referred to as the intercostal muscles 120. A peculiarity of the parasternal muscles in each different intercostal space is that they are innervated separately by a respective intercostal nerve 124. Hence, the inventors have realized that this fact can be exploited for distinguishing between different muscles involved. Due to the fact that the intercostal muscles in each respective intercostal space are innervated separately, the corresponding first and second electromyography signals show uncorrelated signals when the measured electrical activity only originates from the parasternal intercostal muscles. In the anatomical sketch shown in FIG. 4 the transversus thoracis muscle is denoted by reference numeral 126 and the pectoralis major is denoted by reference numeral 128.

FIG. 4 further shows an exemplary embodiment of an electrode patch 2 wherein the first electrode 3A of the first electrode pair will be applied to the skin of the body as a surface electrode for obtaining the first electromyography signal. It can be readily conceived that the first electromyography signal is indicative of an activity of the underlying muscles as seen in FIG. 4 namely the pectoralis major 128, the intercostal muscles 120 as well as the transversus thoracis 126. Hence, the first electromyography signal comprises a superposition of these signals that cannot be easily separated from a single EMG at the second intercostal space 105.

Figure 5:
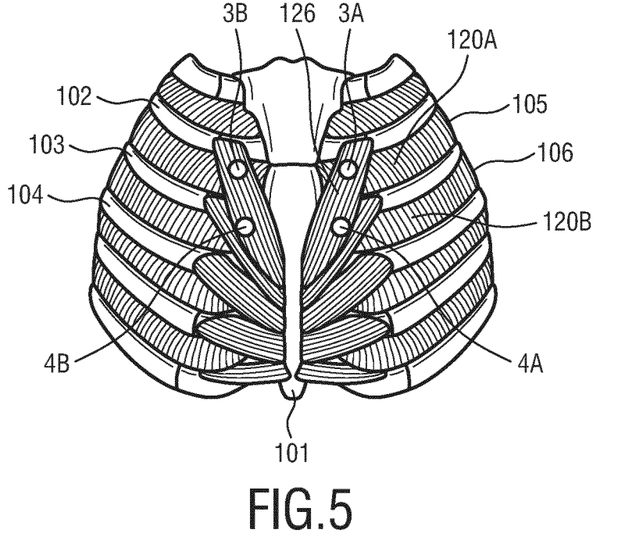
FIG. 5 shows an anatomical sketch of the rib cage for illustrating a relation of the intercostal muscles and the transversus thoracis muscles.

FIG. 5 shows an anatomical sketch of the rib cage of a body 100 as seen from inside the body. A projection of the locations of the first pair of electrodes 3A, 3B for obtaining the first electromyography signals 21 and the second pair of electrodes 4A, 4B for obtaining the second electromyography signal 22 are sketched by circles. As can be seen from FIG. 5, assuming that no contributions of the pectoralis major 128 are present, the first electromyography signal comprises a contribution of the intercostal muscles 120A from the second intercostal space 105 between the second costal 102 and a third costal 103. Correspondingly, the second electromyography signal 22 comprises a contribution from the intercostal muscles 120B from the third intercostal space 106 between the third costal 103 and the fourth costal 104, however not from the second intercostal space. In contrast, the transversus thoracis muscles 126 span across the electrodes 3A, 4A and 3B, 4B of both electrode pairs. Hence, the two differential measurements at the second intercostal space 105 and the third intercostal space 106 will show a correlated signal indicative of an activity of the transversus thoracis muscles 126.

The top muscle bundles from the transversus thoracis run (nearly) vertically from the lower part of the sternum 101 to the second costal 102. The transversus thoracis muscles are just as for the parasternal muscles being innervated via the intercostal nerves.

Figure 6:
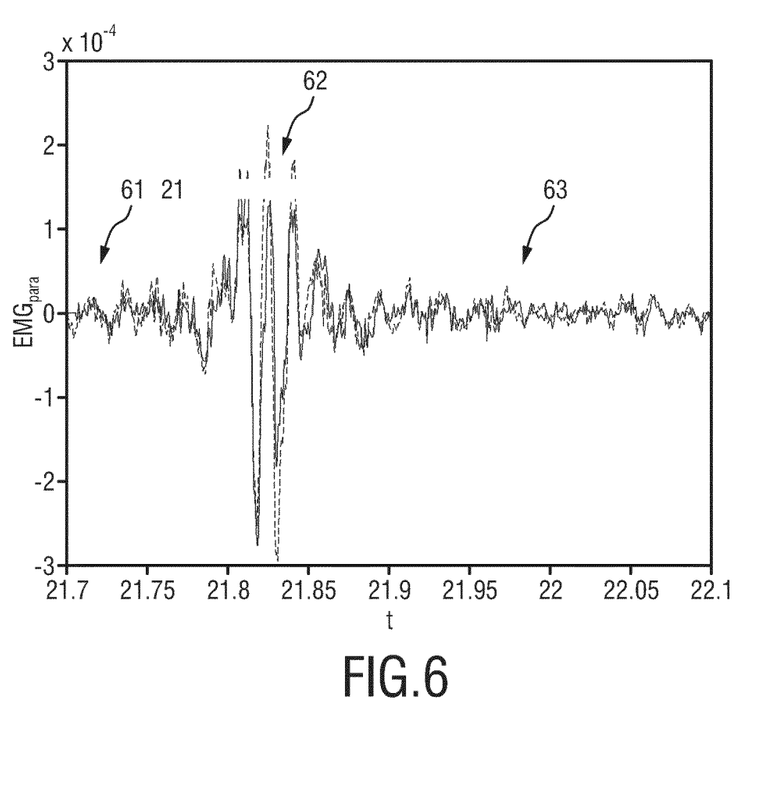
FIG. 6 shows an exemplary graph of a first electromyography signal and a second electromyography signal.
Figure 7A:
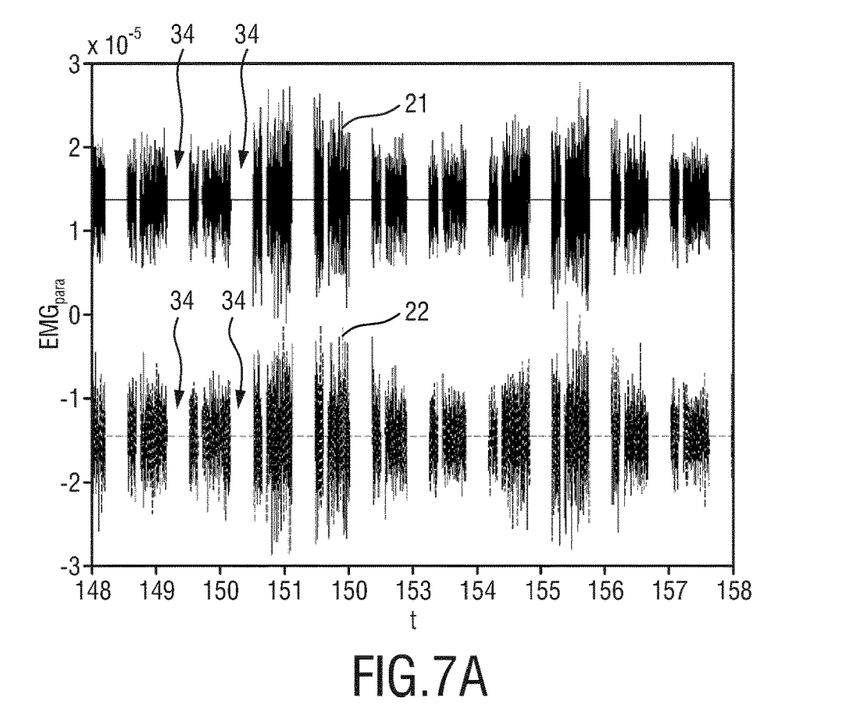
FIGS. 7A and 7B show further graphs of exemplary first and second electromyography signals.
Figure 7B:
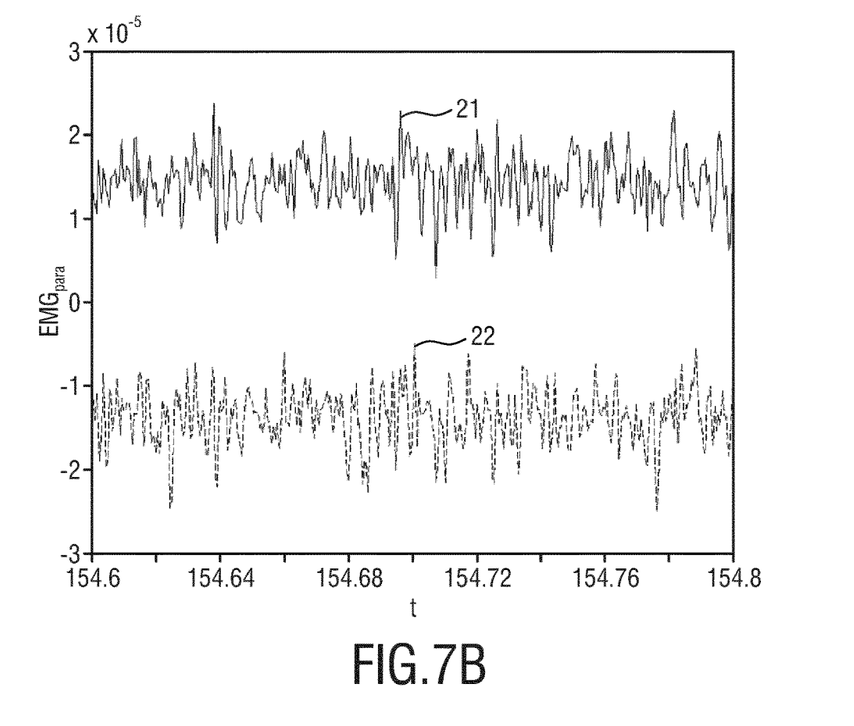

FIGS. 6, 7A and 7B show exemplary graphs of the first and the second electromyography signals 21, 22. The analysis unit 20 receives the first electromyography signal 21 and second electromyography signal 22 and based thereon determines a similarity of the two signals in form of a similarity signal 26. Thereby, the analysis unit 20 is able to distinguish between the inspiratory muscles from the parasternal intercostal muscles and the expiratory muscles from the transversus thoracis muscles as explained above.

FIG. 6 shows an example wherein such a similarity analysis can be used to distinguish coughing, i.e. a forced expiration activity, from an inspiratory activity. It is known that coughing is generated by the transversus thoracis muscle. FIG. 6 shows a first onset of the cough activity 61 which is followed by the maximum activity of the cough 62 which is followed by the decay of the cough activity 63. The solid line corresponds to the first electromyography signal 21 obtained with the first electrode pair 3A, 3B as a first differential measurement signal and the dashed line corresponds to the second electromyography signal 22 as obtained with the second electrode pair 4A, 4B as a second differential measurement signal. As can be seen, the two signals, especially in the lower frequencies, are highly correlated during the maximum activity of the cough. The onset and decay of the cough on the other hand shows a lower similarity.

FIGS. 7A and 7B show traces of the first electromyography signal 21 and the second electromyography signal 22 during quiet breathing. For better graphical representation a vertical offset has been added to the respective signals to more clearly distinguish the signals in FIGS. 7A and 7B. However, both signals should be looked at with a zero average baseline level. FIG. 7A shows the signal after ECG removal by gating wherein signal portions during cardiac activity have been removed as indicated by reference numeral 34. Hence, the QRS complexes 34 indicative of cardiac activity have been removed. In FIG. 7B, a particular selection of FIG. 7A is shown.

Figure 8:
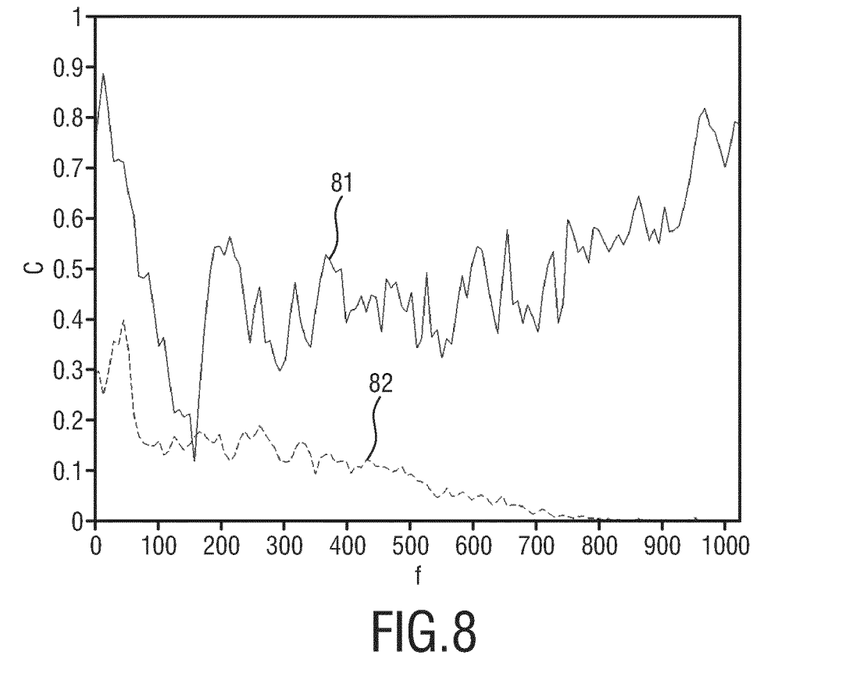
FIG. 8 shows exemplary similarity signals indicative of a spectral coherence between the first and the second electromyography signal when coughing and during quiet breathing.

Referring now to FIG. 8, in the present example, the analysis unit 20 is configured to compute a coherence between the first electromyography signal 21 and a second electromyography signal 22. In FIG. 8, the vertical axis denotes a coherence factor C, whereas the horizontal axis denotes the frequency f. The coherence computed for both coughing and quiet breathing signals is shown in FIG. 8, wherein the curve denoted by reference numeral 81 corresponds to a coughing event 62, whereas curve 82 of much lower coherence corresponds to a period of quiet breathing.

As can be seen from FIG. 8, during coughing, the correlation between the signal from electrode pair 3A, 3B and the correlation between the signal from electrode pair 4A, 4B is not only present for the lower frequencies, but also the higher frequency show much correlation.

Referring again to FIG. 1, the processing apparatus 20 may further comprise an optional second analysis unit 27. The second analysis unit 27 receives the similarity signal 26 from the analysis unit. The second analysis unit 27 is configured to determine, based on the similarity signal 26, a respiratory phase. The second analysis unit can be configured to determine a respiratory phase as an inspiratory phase if the similarity signal obtained from the first and the second electromyography signal is below a first predetermined threshold and/or to determine a respiratory phase as an expiratory phase if the similarity signal obtained from the first and the second electromyography signal exceeds a second predetermined threshold.

The second analysis unit 27 can be further configured to provide, based on the similarity signal, a respiratory phase signal indicative of the respiratory phase; and the processing apparatus can thus be further configured to determine a respiratory effort based on the respiratory phase signal and the first electromyography signal. In particular, the processing apparatus can be configured to determine an inspiratory effort based on a signal energy of the first electromyography signal during an inspiratory phase and/or to determine an expiratory effort based on a signal energy of the first electromyography signal during an expiratory phase.

In addition or in the alternative to determining a similarity signal based on the first electromyography signal and the second electromyography signal, the processing apparatus may be configured for removing from the first electromyography signal a dependent signal that originally is present in both the first electromyography signal and the second electromyography signal. Hence, a cleaned first electromyography signal can be provided. For example, the cleaned first electromyography signal can be indicative of an activity of the parasternal intercostal muscles at the second intercostal space 105, where the electromyography signal is cleaned from the activation of the pectoralis major activity.

Figure 9:
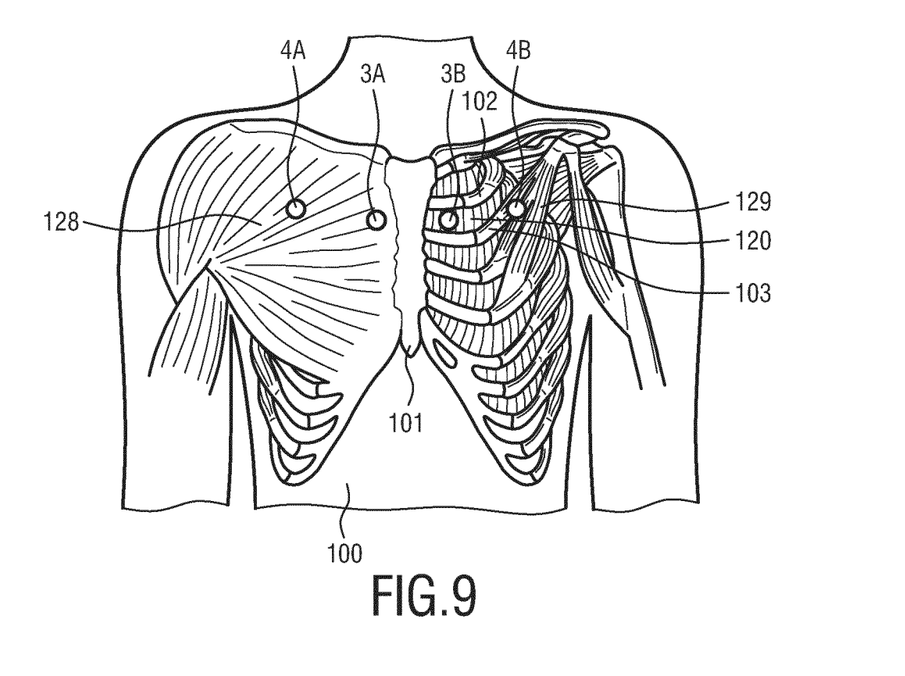
FIG. 9 shows an anatomical sketch with a further EMG electrode configuration.

FIG. 9 shows an anatomical sketch with a further EMG electrode configuration. A projection of the locations of the first pair of electrodes 3A, 3B for obtaining the first electromyography signals 21 and the second pair of electrodes 4A, 4B for obtaining the second electromyography signal 22 are sketched by circles. In this embodiment, the first electrode 3A and second electrode 3B of the first pair of electrodes are applied parasternally on both sides close to the sternum in the second intercostal space 105 between the second costal 102 and the third costal 103 for obtaining the first electromyography signal 21. The third electrode 4A and the fourth electrode 4B of the second pair of electrodes are also applied on both sides of the sternum in the second intercostal space 105, however, further away from the sternum for obtaining the second electromyography signal.

In this embodiment, the second parasternal intercostal muscle 120 is the target muscle, whereas the pectoralis major 128 is the further muscle. The first and second electrode pairs can also be applied at different locations depending on the respective target and further muscles. For example, the third and/or fourth electrode 4A, 4B of the second electrode pair can also be applied at a different location, for example at a different intercostal space, as long as they receive an EMG signal contribution from the further muscle, here the pectoralis major. As shown in FIG. 9, the second pair of electrodes may also measure a contribution from the pectoralis minor 129. The pectoralis minor can thus optionally also be evaluated.

Since the pectoralis major 128 spans over the first and the second pair of electrodes, an activity of the pectoralis major can be seen in both the first electromyography signal 21 and the second electromyography signal 22. Hence, the similarity signal 26, indicative of a similarity between the first electromyography signal and the second electromyography signal, can be indicative of an activity of the pectoralis major. The pectoralis major is typically active during body motion. If not well relaxed, it may also generate some tonic activity. The similarity signal can thus be indicative of a body motion and/or tonic activity.

Advantageously, periods of the first electromyography signal that coincide with such detection of a body motion are discarded. Hence, for example, a neural respiratory drive or breathing effort is not evaluated if the similarity signal exceeds a predetermined threshold. Referring to FIG. 1, the processing apparatus 20 may comprise a second analysis unit 27 which receives the similarity signal 26 and is configured to remove, based on the similarity signal 26, an activity of the further muscle from the first electromyography signal 21. The processing apparatus 20 may remove a signal portion of the first electromyography signal, when an activity of the further muscle is detected. In the alternative, correction or compensation can be applied after detection.

In a further embodiment, the electromyography device 10 of FIG. 1 can be directly applied to the electrode patch 2. Alternatively, the electromyography device 10 may include four (disposable) electrodes that may be clicked on the device after which the device is being attached to the patient at the center of the sternum 101 at the height of the second and third intercostal space 105, 106.

Advantageously, physiological parameters such as respiratory effort or NRD value and/or coughing effort can be monitored continuously and can be wired or wirelessly transmitted by the output unit 18 to a hub such as a patient-monitor or smartphone. Based thereon a clinical assessment can be made. Optionally, smart alarms can be generated, for example by the output unit 18, if a physiological parameter exceeds a threshold value that identifies a possible risk and/or deterioration of the patient.

In conclusion, an advantageous approach for processing electromyography signals is presented. The technical solutions disclosed herein provide a possibility to further improve an electromyography system. In particular, aspects of the proposed solutions provide the possibility to analyze the breathing process in more detail, in particular in COPD patients who increasingly use the inspiratory muscles, including the parasternal intercostal muscles, and the accessory muscles, such as the transversus thoracis muscles to support breathing.

Further aspects are described in the following clauses:

Clause 1: A processing apparatus (20) for processing an electromyography signal indicative of an activity of a target muscle (120) in a human or animal body (100) that relates to the measurement of respiratory effort amid an activity of at least one further muscle (126, 128), comprising: a first interface (23) for receiving a first electromyography signal (21) obtained from the target muscle (120) and the further muscle (126, 128) at a first location on the body (100); a second interface (24) for receiving a second electromyography signal (22) obtained from the further muscle (126, 128) at a second location on the body (100); and an analysis unit (25) for determining a similarity signal (26) based on the first electromyography signal (21) and the second electromyography signal (22).

Clause 2: The processing apparatus according to clause 1, wherein the target muscle (120) is a parasternal intercostal muscle and/or wherein the further muscle is at least one of the transversus thoracis (126) and the pectoralis major (128).

Clause 3: The processing apparatus according to clause 1, wherein said similarity signal (26) is indicative of a correlation or spectral coherence of the first electromyography signal (21) and the second electromyography signal (22).

Clause 4: The processing apparatus according to clause 1, wherein at least one of the first electromyography signal (21) and the second electromyography signal (22) is obtained at an intercostal space (105, 106).

Clause 5: The processing apparatus according to clause 1, wherein the first electromyography signal (21) is obtained at the second intercostal space (105) and/or wherein the second electromyography signal (22) is obtained at the third intercostal space (106).

Clause 6: The processing apparatus according to clause 1, wherein
the first electromyography signal (21) is obtained from the further muscle (126, 128) and a first instance of the target muscle (120A) at the first location on the body; and wherein the second electromyography signal (22) is obtained from the further muscle (126, 128) and a second instance of the target muscle (120B) at the second location on the body.

Clause 7: The processing apparatus according to clause 1, wherein the analysis unit (25) is configured to determine, based on the similarity signal (26), a respiratory phase.

Clause 8: The processing apparatus according to clause 7, wherein the analysis unit (25) is configured to determine a respiratory phase as an inspiratory phase (P2, P3) if the similarity signal (26) obtained from the first and the second electromyography signal (21, 22) is below a first predetermined threshold and/or to determine a respiratory phase as an expiratory phase (P1) if the similarity signal (26) obtained from the first and the second electromyography signal (21, 22) exceeds a second predetermined threshold.

Clause 9: The processing apparatus according to clause 7, wherein the analysis unit (25) is further configured to provide, based on the similarity signal (26), a respiratory phase signal indicative of the respiratory phase; and wherein the processing apparatus (20) is further configured to determine a respiratory effort based on the respiratory phase signal and the first electromyography signal.

Clause 10: The processing apparatus according to clause 9, wherein the processing apparatus (20) is configured to determine an inspiratory effort based on a signal energy of the first electromyography signal (21) during an inspiratory phase and/or to determine an expiratory effort based on a signal energy of the first electromyography signal (21) during an expiratory phase.

Clause 11: The processing apparatus according to clause 1, wherein the processing apparatus (20) is configured to remove, based on the similarity signal (26), an activity of the further muscle (126, 128) from the first electromyography signal (21).

Clause 12: An electrode patch (2) for use with the processing apparatus (20) according to clause 1, the electrode patch (2) comprising at least two sets of electrodes (3A, 3B, 4A, 4B) for surface electromyography measurements at at least two different locations on the chest, wherein a first set of electrodes comprises a first pair of electrodes (3A, 3B) arranged for measuring a first electromyography signal (21) at a first intercostal space (105) besides the sternum (101); and wherein a second set of electrodes comprises a second pair of electrodes (4A, 4B) arranged for measuring a second electromyography signal (22) at a second intercostal space (106) besides the sternum (101).

Clause 13: An electromyography system (1) comprising an electromyography device (10) comprising the processing apparatus (20) according to clause 1; a first pair of electrodes (3A, 3B) for obtaining the first electromyography signal (21), wherein the first pair of electrodes is connectable to a first input (11) of the electromyography device (10) for providing the first electromyography signal (21) to the first interface (23) of the processing apparatus (20); and a second pair of electrodes (4A, 4B) for obtaining the second electromyography signal (22), wherein the second pair of electrodes is connectable to a second input (24) of the electromyography device (10) for providing the second electromyography signal (22) to the second interface (24) of the processing apparatus (20).

Clause 14: Method for processing an electromyography signal indicative of an activity of a target muscle (120) in a human or animal body (100) that relates to the measurement of respiratory effort amid an activity of at least one further muscle (126, 128), the method comprising the steps of: receiving a first electromyography signal (21) obtained from the target muscle (120) and the further muscle (126, 128) at a first location on the body (100); receiving a second electromyography signal (22) obtained from the further muscle (126, 128) at a second location on the body (100); and determining a similarity signal (26) based on the first electromyography signal (21) and the second electromyography signal (22).

Clause 15: Computer program comprising program code means for causing a computer to carry out the steps of the method as described in clause 14 when said computer program is carried out on a computer.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A processing apparatus for processing an electromyography signal indicative of an activity of a target muscle in a human or animal body that relates to a measurement of respiratory effort amid an activity of at least one further muscle, comprising:

a first electrode interface within an electromyography device, the first electrode interface configured to receive a first electromyography signal obtained from the target muscle and the further muscle at a first location on the body, wherein the target muscle and the further muscle are innervated separately;

a second electrode interface within the electromyography device, the second electrode interface configured to receive a second electromyography signal obtained from the further muscle at a second location on the body; and a processor within the electromyography device, the processor configured to determine a similarity signal based on a similarity between the first electromyography signal and the second electromyography signal, wherein the processor is further configured to:

determine a respiratory phase as an inspiratory phase if the similarity signal obtained from the first and the second electromyography signal is below a first predetermined threshold; and determine the respiratory phase as an expiratory phase if the similarity signal obtained from the first and the second electromyography signal exceeds a second predetermined threshold; and wherein the processor is further configured to control an output to visualize the inspiratory phase or the expiratory phase and generate an alarm if a physiological parameter associated with the inspiratory phase or the expiratory phase exceeds a threshold value.

2. The processing apparatus according to claim 1, wherein the target muscle is a parasternal intercostal muscle and/or wherein the further muscle is at least one of the transversus thoracis and the pectoralis major.

3. The processing apparatus according to claim 1, wherein said similarity signal is indicative of a correlation or spectral coherence of the first electromyography signal and the second electromyography signal.

4. The processing apparatus according to claim 1, wherein at least one of the first electromyography signal and the second electromyography signal is obtained at an intercostal space.

5. The processing apparatus according to claim 1, wherein the first electromyography signal is obtained at a second intercostal space and/or wherein the second electromyography signal is obtained at a third intercostal space.

6. The processing apparatus according to claim 1, wherein:
the first electromyography signal is obtained from the further muscle and a first instance of the target muscle at the first location on the body; and
the second electromyography signal is obtained from the further muscle and a second instance of the target muscle at the second location on the body.

7. The processing apparatus according to claim 1,
wherein the processor is further configured to provide, based on the similarity signal, a respiratory phase signal indicative of the respiratory phase; and
wherein the processing apparatus is further configured to determine a respiratory effort based on the respiratory phase signal and the first electromyography signal.

8. The processing apparatus according to claim 7,
wherein the processing apparatus is configured to determine an inspiratory effort based on a signal energy of the first electromyography signal during the inspiratory phase and/or to determine an expiratory effort based on a signal energy of the first electromyography signal during the expiratory phase.

9. The processing apparatus according to claim 1, wherein the processing apparatus is configured to remove, based on the similarity signal, an activity of the further muscle from the first electromyography signal.

10. An electrode patch for use with the processing apparatus according to claim 1, the electrode patch comprising at least two sets of electrodes arranged for surface electromyography measurements at at least two different locations on the chest,
wherein a first set of electrodes comprises a first pair of electrodes arranged for measuring the first electromyography signal at a first intercostal space besides the sternum; and
wherein a second set of electrodes comprises a second pair of electrodes arranged for measuring the second electromyography signal at a second intercostal space besides the sternum.

11. A processing apparatus for processing an electromyography signal indicative of an activity of a target muscle in a human or animal body that relates to a measurement of respiratory effort amid an activity of at least one further muscle, comprising:
a first electrode interface within an electromyography device, the first electrode interface configured to receive a first electromyography signal obtained from the target muscle and the further muscle at a first location on the body;
a second electrode interface within the electromyography device, the second electrode interface configured to receive a second electromyography signal obtained from the further muscle at a second location on the body;
a processor within the electromyography device, the processor configured to determine a similarity signal based on a similarity between the first electromyography signal and the second electromyography signal;
wherein the processor is further configured to provide, based on the similarity signal, a respiratory phase signal indicative of an inspiratory phase and an expiratory phase; and
wherein the processing apparatus is further configured to determine a respiratory effort based on the respiratory phase signal and the first electromyography signal; and
wherein the processor is further configured to control an output to visualize the inspiratory phase and the expiratory phase and generate an alarm if a physiological parameter associated with the inspiratory phase or the expiratory phase exceeds a threshold value.

12. The processing apparatus according to claim 11,
wherein the processing apparatus is configured to determine an inspiratory effort based on a signal energy of the first electromyography signal during the inspiratory phase and/or to determine an expiratory effort based on a signal energy of the first electromyography signal during the expiratory phase.

13. An electromyography system, comprising:
the electromyography device comprising the processing apparatus according to claim 11;
a first pair of electrodes arranged for obtaining the first electromyography signal, wherein the first pair of electrodes is connectable to a first input of the electromyography device for providing the first electromyography signal to the first interface of the processing apparatus; and
a second pair of electrodes arranged for obtaining the second electromyography signal, wherein the second pair of electrodes is connectable to a second input of the electromyography device for providing the second electromyography signal to the second interface of the processing apparatus.

14. A method for processing an electromyography signal indicative of an activity of a target muscle in a human or animal body that relates to a measurement of respiratory effort amid an activity of at least one further muscle, the method comprising the steps of:
receiving, by a first electrode interface within an electromyography device, a first electromyography signal obtained from the target muscle and the further muscle at a first location on the body, wherein the target muscle and the further muscle are innervated separately;
receiving, by a second electrode interface within the electromyography device, a second electromyography signal obtained from the further muscle at a second location on the body;
determining, by a processor within the electromyography device, a similarity signal based on a similarity between the first electromyography signal and the second electromyography signal; and
determining, by the processor, a respiratory phase as an inspiratory phase if the similarity signal obtained from the first and the second electromyography signal is below a first predetermined threshold and/or
determining, by the processor, the respiratory phase as an expiratory phase if the similarity signal obtained from the first and the second electromyography signal exceeds a second predetermined threshold;
controlling an output to visualize the inspiratory phase or the expiratory phase or generating an alarm if a physiological parameter associated with the inspiratory phase or the expiratory phase exceeds a threshold value.

15. A method for processing an electromyography signal indicative of an activity of a target muscle in a human or animal body that relates to a measurement of respiratory effort amid an activity of at least one further muscle, the method comprising the steps of:
receiving, by a first electrode interface within an electromyography device, a first electromyography signal obtained from the target muscle and the further muscle at a first location on the body, wherein the target muscle and the further muscle are innervated separately;
receiving, by a second electrode interface within the electromyography device, a second electromyography signal obtained from the further muscle at a second location on the body;
determining, by a processor within the electromyography device, a similarity signal based on a similarity between the first electromyography signal and the second electromyography signal; and
providing, by the processor, based on the similarity signal, a respiratory phase signal indicative of a respiratory phase; and determining, by the processor, a respiratory effort based on the respiratory phase signal and the first electromyography signal;
controlling an output to visualize the respiratory phase or generating an alarm if a physiological parameter associated with the respiratory phase exceeds a threshold value.

16. Computer program comprising program code means for causing a computer to carry out the steps of the method as claimed in claim 14 when said computer program is carried out on a computer.

\* \* \* \* \*